United States Patent [19]

Koyama et al.

[11] Patent Number: 5,596,118
[45] Date of Patent: Jan. 21, 1997

[54] METHOD FOR THE PREPARATION OF ORGANOXY-FUNCTIONAL SILANES

[75] Inventors: Taku Koyama; Yasushi Sugiura, both of Chiba Prefecture, Japan

[73] Assignee: Dow Corning Toray Silicone Co., Ltd., Tokyo, Japan

[21] Appl. No.: 564,767

[22] Filed: Nov. 29, 1995

[30] Foreign Application Priority Data

Nov. 29, 1994 [JP] Japan ................................ 6-319104
Nov. 29, 1994 [JP] Japan ................................ 6-319105

[51] Int. Cl.$^6$ ........................... C07F 7/08; C07F 7/18
[52] U.S. Cl. ........................................................... 556/471
[58] Field of Search ................................................. 556/471

[56] References Cited

U.S. PATENT DOCUMENTS 4,173,576  11/1979  Seiler et al. ............................ 556/471
4,851,558  7/1989  Nishida et al. ......................... 556/471
5,493,044  2/1996  Schwindemann ...................... 556/471

OTHER PUBLICATIONS

Patai, S. "The Chemistry of orgnaic silicon compounds" 1989, pp. 725–729.

*Primary Examiner*—Paul F. Shaver
*Attorney, Agent, or Firm*—Arne R. Jarnholm

[57] ABSTRACT

The production of organoxy-functional silanes is carried out by the reaction of (A) halosilanes and (B) hydroxy compounds in the presence of (C) a polymer that includes carbon-bonded fluorine. The presence of (C), the polymer that includes carbon-bonded fluorine, acts to decrease foaming during the reaction and minimizes the production of siloxane oligomer by-products.

11 Claims, No Drawings

METHOD FOR THE PREPARATION OF ORGANOXY-FUNCTIONAL SILANES

BACKGROUND OF THE INVENTION

1. Field of the Invention

The present invention relates generally to a method for preparing organoxy-functional silanes and more particularly to a novel method for such production which utilizes the reaction of halosilanes and hydroxy compounds in the presence of a polymer that includes carbon-bonded fluorine.

2. Description of the Prior Art

Organoxy-functional silanes, for example alkoxysilanes and phenoxysilanes, are in wide use as water repellents and surface-treatment agents. This class of compounds has heretofore been prepared mainly by the reaction (dehydrohalogenation) between a halosilane and a hydroxy compound. The halosilane precursor has been synthesized, for example, by the direct reaction of halohydrocarbon with silicon metal, the reaction of silicon metal with hydrogen halide, and catalyzed hydrosilylation between alkenes and SiH-functional halosilanes.

One drawback to this method for the preparation of organoxy-functional silane is associated with the vigorous foaming that can occur during the dehydrohalogenation reaction due to the evolved hydrogen halide gas and volatilized hydroxy compound. This has made it necessary to reduce the per-unit timefeed of hydroxy compound to the reactor, which hinders productivity.

BRIEF SUMMARY OF THE INVENTION

In accordance with the present invention there is provided a method for the preparation of organoxy-functional silanes having the following general formula

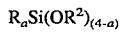

wherein each R is a monovalent hydrocarbon radical, which R groups may be the same or different, $R^2$ is a substituted or unsubstituted monovalent hydrocarbon radical, and a is an integer with a value from 0 to 3, said method comprising the step of reacting:

(A) a halosilane having the general formula $R_aSiX_{(4-a)}$ wherein R and a are defined as above and X is a halogen atom; and (B) a hydroxy compound having the general formula $R^2OH$ wherein $R^2$ is defined as above; said reacting step being carried out in the presence of (C) a polymer which includes carbon-bonded fluorine.

The present inventors have discovered that the reaction of the above-described (A) halosilane and (B) hydroxy compound in the presence of the (C) polymer which includes carbon-bonded fluorine, suppresses foaming during the reaction and yields a very pure organoxy-functional silane by reducing the production of siloxane oligomers, a reaction by-product, to low levels.

DETAILED DESCRIPTION OF THE INVENTION

The halosilane used as component (A) in the present invention represents the starting point for the production organoxy-functional silanes. Component (A) has the general formula: $R_aSi(OR^2)_{(4-a)}$, where R represents monovalent hydrocarbon radicals, for example, alkyl radicals such as methyl, ethyl, propyl and butyl, and aryl radicals such as phenyl and tolyl. C1 to C30 monovalent hydrocarbon radicals are preferred for R. X is a halogen atom, such as chlorine or bromine but chlorine is preferred. The subscript a is an integer with a value from zero to 3.

Suitable halosilanes (A) include tetrachlorosilane, methyltrichlorosilane, dimethyldichlorosilane, trimethylchlorosilane, ethyltrichlorosilane, ethylmethyldichlorosilane, ethyldimethylchlorosilane, propyltrichlorosilane, propylmethyldichlorosilane, propyldimethylchlorosilane, butyltrichlorosilane, butylmethyldichlorosilane, butyldimethylchlorosilane, hexyltrichlorosilane, hexylmethyldichlorosilane, hexyldimethylchlorosilane, octyltrichlorosilane, octylmethyldichlorosilane, octyldimethylchlorosilane, decyltrichlorosilane, decylmethyldichlorosilane, decyldimethylchlorosilane, dodecyltrichlorosilane, dodecylmethyldichlorosilane, dodecyldimethylchlorosilane, tetradecyltrichlorosilane, tetradecylmethyldichlorosilane, tetradecyldimethylchlorosilane, hexadecyltrichlorosilane, hexadecylmethyldichlorosilane, hexadecyldimethylchlorosilane, octadecyltrichlorosilane, octadecylmethyldichlorosilane, octadecyldimethylchlorosilane, eicosyltrichlorosilane, eicosylmethyldichlorosilane, eicosyldimethylchlorosilane, triacontyltrichlorosilane, triacontylmethyldichlorosilane, triacontyldimethylchlorosilane, vinyltrichlorosilane, vinylmethyldichlorosilane, vinyldimethylchlorosilane, allyltrichlorosilane, allylmethyldichlorosilane, allyldimethylchlorosilane, 5-hexenyltrichlorosilane, 5-hexenylmethyldichlorosilane, 5-hexenyldimethylchlorosilane, phenyltrichlorosilane, phenylmethyldichlorosilane, phenyldimethylchlorosilane, diphenyldichlorosilane, methyldiphenylchlorosilane and triphenylchlorosilane.

The hydroxy compound used as component (B) in the method of the present invention has the general formula $R^2OH$, wherein $R^2$ denotes substituted and unsubstituted monovalent hydrocarbon radicals. Suitable $R^2$ radicals include: alkyl radicals such as methyl, ethyl and propyl; aryl radicals such as phenyl and tolyl; alkenyl radicals such as allyl; and by the preceding radicals in which part of the hydrogen has been replaced by an alkoxy radical, e.g., methoxy or ethoxy or by a halogen atom, e.g., chlorine or fluorine. Thus, suitable hydroxy compounds of component (B) include methanol, ethanol, propanol, butanol, hexanol, octanol, decanol, dodecanol, allyl alcohol, phenol, phenethyl alcohol and methoxyethanol.

Component (C) of the present invention is a polymer which includes carbon-bonded fluorine. This component functions both to inhibit the foam that is produced by prior art methods during the reaction of components (A) and (B) and to inhibit the siloxane oligomers, a reaction by-product. No particular restrictions apply to the composition or structure of component (C), so long as it is a polymer that contains carbon-bonded fluorine. To facilitate handling, it is preferable that component (C) be a solid or liquid at ambient temperatures and the temperature at which the reaction is carried out.

Suitable compounds for use as component (C) include fluorine-containing silicone resins and solid powders, such as silica, wherein the surface of such inert powders has been coated or treated with such a fluorine-containing polymer.

Other examples include fluoropolymers such as polytetrafluoroethylene, polytrifluorochloroethylene, polyvinyl fluoride, polyvinylidene fluoride, which are available commercially.

Further examples of component (C) include alpha,omega-trimethylsiloxy-endblocked 3,3,3-trifluoropropylmethylpolysiloxane, 3,3,3-trifluoropropylmethylcyclopolysiloxane, and low-polymeric ethylene trifluoride resins. These fluorine-containing polymers are also available commercially.

Component (C) is generally added at from 0.0001 to 100 weight parts per 100 weight parts halosilane (A) and is preferably added at from 0.0001 to 10 weight parts per 100 weight parts halosilane (A).

The method of the invention comprises reacting the above-described components (A) and (B) in the presence of component (C) at a predetermined reaction temperature. Any reaction temperature may be used at which the dehydrohalogenation reaction between components (A) and (B) will run. The reaction temperature will generally fall in the range from −78° C. to 200° C. and preferably ranges from 0° C. to 150° C.

Similarly, any reaction pressure may be used at which the dehydrohalogenation reaction between components (A) and (B) will run. Typical reaction pressures will generally fall in the range from 0.001 to 10 arm and preferably falls in the range from 0.001 to 3 arm.

Generally stated, the invention method for preparing organoxy-functional silanes comprises the reaction of the above-described components (A) and (B) in the presence of component (C). More specifically, the reaction itself will typically be implemented, for example, by feeding (B) into a mixture of components (A) and (C) or by simultaneously or sequentially feeding (A) and (B) into the presence of component (C).

EXAMPLES

In the following examples of the invention and comparative examples, all references to %, unless otherwise specifically stated, are weight %.

Example 1

The following were introduced into a cylindrical 1000-mL four-neck separable flask equipped with a mechanical stirrer, condenser, and addition funnel and were heated to 60° C.: 137.9 g (0,500 mole) decyltrichlorosilane and 0.70 g of a powdered fluorosilicone resin with the average component formula $C_8F_{17}CH_2CH_2SiO_{3/2}$. Then, while maintaining the same temperature, 48.0 g methanol was gradually added dropwise over a period of 30 minutes. The reaction was run at 1 arm. Only an extremely small amount of microfine foam was observed to be produced by the reaction. Moreover, this foam did not cover more than 10% of the surface of the reaction solution. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 123.3 g reaction product.

Analysis of the reaction product by gas chromatography confirmed that its main component was decyltrimethoxysilane. Its purity was 98.1% and it contained 1.0% siloxane dimer. The reaction product was distilled under reduced pressure and the fraction at bp 110° C./7 mmHg was collected. The yield was 111.0 g or 84.5%, and the purity was 99.9%. These results are reported in Table 1 below.

Example 2

The following were introduced into a cylindrical 1000-mL four-neck separable flask equipped with a mechanical stirrer, condenser, and addition funnel and were heated to 60° C: 137.9 g (0.500 mole) decyltrichlorosilane and 1.40 g polytetrafluoroethylene powder (catalogue number 18,247-8, from the Aldrich Chemical Company). Then, while maintaining the same temperature, 48.0 g methanol was gradually added dropwise over a period of 30 minutes. The reaction was run at 1 atm. Only an extremely small amount of microfine foam was observed to be produced by the reaction. Moreover, this foam did not cover more than 10% of the surface of the reaction solution. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 124.8 g reaction product.

Analysis of the reaction product by gas chromatography confirmed that its main component was decyltrimethoxysilane. Its purity was 93.8% and it contained 3.9% siloxane dimer. The reaction product was distilled under reduced pressure and the fraction at bp 110° C./7 mmHg was collected. The yield was 104.5 g or 79.5%, and the purity was 99.9%. These results are reported in Table 1 below.

Example 3

The following were introduced into a cylindrical 1000-mL four-neck separable flask equipped with a mechanical stirrer, condenser, and addition funnel and were heated to 60° C.: 137.9 g (0.500 mole) decyltrichlorosilane and 0.69 g of a silica powder (brand name: Wakogel C-200, product of Wako Junyaku Kabushiki Kaisha) whose surface had been treated with $n\text{-}C_8F_{17}CH_2CH_2Si\,(OCH_2CH_3)_3$. Then, while maintaining the same temperature, 48.0 g methanol was gradually added dropwise over a period of 30 minutes. The reaction was run at 1 atm. Only an extremely small amount of microfine foam was observed to be produced by the reaction. Moreover, this foam did not cover more than 10% of the surface of the reaction solution. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 129.5 g reaction product.

Analysis of this reaction product by gas chromatography confirmed that its main component was decyltrimethoxysilane. Its purity was 94.6% and it contained 2.4% siloxane dimer. The reaction product was distilled under reduced pressure and the fraction at bp 110° C./7 mmHg was collected. The yield was 108.7 g or 82.7%, and the purity was 99.9%. These results are reported in Table 1 below.

Example 4

The following were introduced into a cylindrical 1000-mL four-neck separable flask equipped with a mechanical stirrer, condenser, and addition funnel and were heated to 30° C.: 253.2 g (1.00 mole) diphenyldichlorosilane and 0.70 g of a powdered fluorosilicone resin with the average component formula $C_8F_{17}CH_2CH_2SiO_{3/2}$. Then, while maintaining the same temperature, 64.0 g methanol (2.00 moles) was gradually added dropwise over a period of 60 minutes. The reaction was run at 1 arm. Only an extremely small amount of microfine foam was observed to be produced by the reaction. Moreover, this foam did not cover more than 10% of the surface of the reaction solution. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 223.8 g reaction product.

Analysis of the reaction product by gas chromatography confirmed that its main component was diphenyldimethoxysilane. Its purity was 97.2% and it contained 1.7% siloxane dimer. The reaction product was distilled under reduced pressure and the fraction at bp 120° C./8 mmHg was collected. The yield was 201.8 g or 82.5%, and the purity was 99.9%. These results are reported in Table 1 below.

Example 5

The following were introduced into a cylindrical 1000-mL four-neck separable flask equipped with a mechanical stirrer, condenser, and addition funnel and were heated to 80° C.: 176.2 g (0.750 mole) decyldimethylchlorosilane and 0.18 g of a powdered fluorosilicone resin with the average component formula $C_8F_{17}CH_2CH_2SiO_{3/2}$. Then, while maintaining the same temperature, 24.0 g methanol (0.75 mole) was gradually added dropwise over a period of 60 minutes. The reaction was run at 1 atm. Only an extremely small amount of microfine foam was observed to be produced by the reaction. Moreover, this foam did not cover more than 10% of the surface of the reaction solution. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 151.9 g reaction product.

Analysis of the reaction product by gas chromatography confirmed that its main component was decyldimethylmethoxysilane. Its purity was 85.2% and it contained 12.8% siloxane dimer. The reaction product was distilled under reduced pressure and the fraction at bp 120° C./8 mmHg was collected. The yield was 116.5 g or 66.2%, and the purity was 98.2%. These results are reported in Table 1 below.

Example 6

The following were introduced into a cylindrical 1000-mL four-neck separable flask equipped with a mechanical stirrer, condenser, and addition funnel and were heated to 60° C.: 64.5 g (0.500 mole) dimethyldichlorosilane and 0.65 g of a powdered fluorosilicone resin with the average component formula $C_8F_{17}CH_2CH_2SiO_{3/2}$. Then, while maintaining the same temperature, 45.0 g ethanol (1.00 mole) was gradually added dropwise over a period of 30 minutes. The reaction was run at 1 atm. Only an extremely small amount of microfine foam was observed to be produced by the reaction. Stirring was carried out for an additional 30 minutes after the completion of ethanol addition. The reaction was concluded by cooling the reaction solution to 30° C. and neutralization with 20% ethanolic sodium ethoxide solution. Distillation of the ethanol under reduced pressure and filtration of the salt product gave 70.0 g reaction product.

Analysis of the reaction product by gas chromatography confirmed that its main component was dimethyldiethoxysilane. Its purity was 97.7% and it contained 1.1% siloxane dimer. The reaction product was distilled under reduced pressure and the fraction at bp 110° C. was collected. The yield was 62.8 g or 84.6%, and the purity was 99.9%. These results are reported in Table 1 below.

Example 7

The following were introduced into a cylindrical 1000-mL four-neck separable flask equipped with a mechanical stirrer, condenser, and addition funnel and were heated to 60° C.: 137.9 g (0.500 mole) decyltrichlorosilane and 13.8 g of an alpha, omega-trimethylsiloxy-endblocked 3,3,3-trifluoropropylmethylpolysiloxane with a viscosity at 25° C. of 100 centistokes. Then, while maintaining the same temperature, 48.0 g (1.50 moles) methanol was gradually added dropwise over a period of 30 minutes. The reaction was run at 1 atm. Only an extremely small amount of microfine foam was observed to be produced by the reaction. Moreover, this foam did not cover more than 20% of the surface of the reaction solution. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 128.8 g reaction product.

Analysis of the reaction product by gas chromatography confirmed that its main component was decyltrimethoxysilane. Its purity was 94.3% and it contained 3.2% siloxane dimer. The reaction product was distilled under reduced pressure and the fraction at bp 110° C./7 mmHg was collected. The yield was 105.2 g or 80.1%, and the purity was 99.9%. These results are reported in Table 1 below.

Example 8

The following were introduced into a cylindrical 1000-mL four-neck separable flask equipped with a mechanical stirrer, condenser, and addition funnel and were heated to 60° C.: 137.9 g (0.500 mole) decyltrichlorosilane and 1.40 g low-polymeric ethylene trifluoride resin (viscosity at 25° C.=200 centistokes, brand name: FL800, product of Asahi Glass Company, Limited). Then, while maintaining the same temperature, 48.0 g methanol (1.00 mole) was gradually added dropwise over a period of 30 minutes. The reaction was run at 1 atm. Only an extremely small amount of microfine foam was observed to be produced by the reaction. Moreover, this foam did not cover more than 20% of the surface of the reaction solution. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 124.8 g reaction product.

Analysis of this reaction product by gas chromatography confirmed that its main component was decyltrimethoxysilane. Its purity was 94.2% and it contained 2.3% siloxane dimer. The reaction product was distilled under reduced pressure and the fraction at bp 110° C./7 mmHg was collected. The yield was 107.3 g or 81.7%, and the purity was 99.9%. These results are reported in Table 1 below.

Example 9

The following were introduced into a cylindrical 1000-mL four-neck separable flask equipped with a mechanical stirrer, condenser, and addition funnel and were heated to 60° C.: 64.5 g (0.500 mole) dimethyldichlorosilane and 0.65 g low-polymeric ethylene trifluoride resin (viscosity at 25° C.=200 centistokes, brand name: FL800, product of Asahi Glass Company, Limited). Then, while maintaining the same temperature, 45.0 g ethanol was gradually added dropwise over a period of 30 minutes. The reaction was run at 1 atm. Only an extremely small amount of microfine foam was observed to be produced by the reaction. Stirring was carried out for an additional 30 minutes after the completion of ethanol addition. The reaction was concluded by cooling the reaction solution to 30° C. and neutralization with 20% ethanolic sodium ethoxide solution. Distillation of the ethanol under reduced pressure and filtration of the salt product gave 69.4 g reaction product.

Analysis of the reaction product by gas chromatography confirmed that its main component was dimethyldiethoxysilane. Its purity was 96.7% and it contained 1.8% siloxane dimer. The reaction product was distilled under reduced pressure and the fraction at bp 110° C./7 mmHg was collected. The yield was 62.2 g or 83.8%, and the purity was 99.9%. These results are reported in Table 1 below.

Comparative Example 1

137.9 g (0.500 mole) decyltrichlorosilane was introduced into a cylindrical 1000-mL four-neck separable flask equipped with a mechanical stirrer, condenser, and addition funnel and heated to 60° C. Then, while maintaining the same temperature, 48.0 g methanol (1.50 moles) was gradually added dropwise over a period of 60 minutes. The reaction was run at 1 atm. The foaming due to the reaction reached a maximum of 670% of the liquid fraction of the reaction mixture. This foaming was quite vigorous, and twice the time was required as compared to Example 1. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 128.8 g reaction product.

Analysis of the reaction product by gas chromatography confirmed that its main component was decyltrimethoxysilane. Its purity was 83.8% and it contained 11.7% siloxane dimer. The reaction product was distilled under reduced pressure and the fraction at bp 110° C./7 mmHg was collected. The yield was 88.3 g or 67.2%, and the purity was 99.9%. These results are reported in Table 2 below.

Comparative Example 2

The following were introduced into a cylindrical 1000-mL four-neck separable flask equipped with a mechanical stirrer, condenser, and addition funnel and were heated to 60° C.: 137.9 g (0.500 mole) decyltrichlorosilane and 13.8 g of an alpha, omega-trimethylsilyl-endblocked dimethylsilicone oil with a kinematic viscosity of 1000 cSt. Then, while maintaining the same temperature, 48.0 g methanol (1.50 moles) was gradually added dropwise over a period of 60 minutes. The reaction was run at 1 atm. The foaming due to the reaction reached a maximum of 1200% of the liquid fraction of the reaction mixture. This foaming was quite vigorous, and twice the time was required as compared to Example 1. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 123.1 g reaction product.

Analysis of this reaction product by gas chromatography confirmed that its main component was decyltrimethoxysilane. Its purity was 82.7% and it contained 13.5% siloxane dimer. The reaction product was distilled under reduced pressure and the fraction at bp 110° C./7 mmHg was collected. The yield was 70.2 g or 53.4% and the purity was 99.9%. These results are reported Comparative Example 3

The following were introduced into a cylindrical 1000-mL four-neck separable flask equipped with a mechanical stirrer, condenser, and addition funnel and were heated to 60° C.: 137.9 g (0.500 mole) decyltrichlorosilane and 1.32 g silica powder (brand name: Wakogel C-200, product of Wako Junyaku Kabushiki Kaisha). Then, while maintaining the same temperature, 48.0 g methanol (1.50 moles) was gradually added dropwise over a period of 60 minutes The reaction was run at 1 atm. The foaming due to the reaction reached a maximum of 600% of the liquid fraction of the reaction mixture. This foaming was quite vigorous, and twice the time was required as compared to Example 1. Stirring was carried out for an additional 30 minutes after the completion of methanol addition The reaction was concluded by cooling the reaction solution to 30° C. and neutralization with 28% methanolic sodium methoxide solution Distillation of the methanol under reduced pressure and filtration of the salt product gave 128.5 g reaction product.

Analysis of the reaction product by gas chromatography confirmed that its main component was decyltrimethoxysilane. Its purity was 82.7% and it contained 13.0% siloxane dimer. The reaction product was distilled under reduced pressure and the fraction at bp 110° C./7 mmHg was collected. The yield was 74.3 g or 56.6%, and the purity was 99.9%. These measurement results are reported in Table 2 below.

Comparative Example 4

253.2 g (1.00 mole) diphenyldichlorosilane was introduced into a cylindrical 1000-mL four-neck separable flask equipped with a mechanical stirrer, condenser, and addition funnel and was heated to 30° C. Then, while maintaining the same temperature, 64.0 g methanol (2.00 moles) was gradually added dropwise over a period of 60 minutes. The reaction was run at 1 arm. Only an extremely small amount of microfine foam was observed to be produced by the reaction. This foam did not cover more than 50% of the surface of the reaction solution. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 197.7 g reaction product.

Analysis of the reaction product by gas chromatography confirmed that its main component was diphenyldimethoxysilane. Its purity was 79.8% and it contained 19.0% siloxane dimer. The reaction product was distilled under reduced pressure and the fraction at bp 120° C./8 mmHg was collected. The yield was 132.6 g or 54.2%, and the purity was 99.9%. These results are reported in Table 2 below.

Comparative Example 5

176.2 g (0.750 mole) decyldimethylchlorosilane was introduced into a cylindrical 1000-mL four-neck separable flask equipped with a mechanical stirrer, condenser, and addition funnel and was heated to 80° C. Then, while operating at the same temperature, 24.0 g methanol (0.75 mole) was gradually added dropwise over a period of 60 minutes. The reaction was run at 1 atm. Only an extremely small amount of microfine foam was observed to be produced by the reaction. Moreover, this foam did not cover more than 10% of the surface of the reaction solution. Stirring was carried out for an additional 30 minutes after the completion of methanol addition. The reaction was concluded by cooling the reaction solution to 30° C. and neutralization with 28% methanolic sodium methoxide solution. Distillation of the methanol under reduced pressure and filtration of the salt product gave 142.9 g reaction product.

Analysis of the reaction product by gas chromatography confirmed that its main component was decyldimethylmethoxysilane. Its purity was 44.1% and it contained 52.0% siloxane dimer. The reaction product was distilled under reduced pressure and the fraction at bp 120° C./8 mmHg was collected. The yield was 56.8 g or 32.2%, and the purity was 98.0%. These results are reported in Table 1 below.

TABLE 1

|  | maximum amount foaming (%) | after completion of the reaction | | after distillation | |
| --- | --- | --- | --- | --- | --- |
|  |  | purity (%) | siloxane dimer (%) | purity (%) | yield (%) |
| Example 1 | (10% of surface) | 98.1 | 1.0 | 99.9 | 84.5 |
| Example 2 | (10% of surface) | 93.8 | 3.9 | 99.9 | 79.5 |
| Example 3 | (10% of surface) | 94.6 | 2.4 | 99.9 | 82.7 |
| Example 4 | (10% of surface) | 97.2 | 1.7 | 99.9 | 82.5 |
| Example 5 | (10% of surface) | 85.2 | 12.8 | 98.2 | 66.2 |
| Example 6 | (10% of surface) | 97.7 | 1.1 | 99.9 | 84.6 |
| Example 7 | (20% of surface) | 94.3 | 3.2 | 99.9 | 80.1 |
| Example 8 | (20% of surface) | 94.2 | 2.3 | 99.9 | 81.7 |
| Example 9 | trace | 96.7 | 1.8 | 99.9 | 83.8 |

TABLE 2

|  | maximum amount foaming (%) | after completion of the reaction | | after distillation | |
| --- | --- | --- | --- | --- | --- |
|  |  | purity (%) | siloxane dimer (%) | purity (%) | yield (%) |
| Comparative Example 1 | 670% | 83.8 | 11.7 | 99.9 | 67.2 |
| Comparative Example 2 | 1200% | 82.7 | 13.5 | 99.9 | 53.4 |
| Comparative Example 3 | 600% | 82.7 | 13.0 | 99.9 | 56.6 |
| Comparative Example 4 | (50% of surface) | 79.8 | 19.0 | 99.9 | 54.2 |
| Comparative Example 5 | (10% of surface) | 44.1 | 52.0 | 98.0 | 32.2 |

The method of the present invention, and the features and advantages thereof, have been explained by way of the preceding examples and comparisons to methods of the prior art. The scope of the present invention is not, however, limited thereby and should be judged only in accordance with the following claims and equivalents thereof.

What is claimed is:

1. A method for the preparation of organoxy-functional silanes having the following general formula

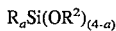

$R_a Si(OR^2)_{(4-a)}$ wherein each R is a monovalent hydrocarbon radical, which R groups may be the same or different, $R^2$ is a substituted or unsubstituted monovalent hydrocarbon radical, and a is an integer with a value from 0 to 3, said method comprising the step of reacting:

(A) a halosilane having the general formula $R_1 SiX_{(4-a)}$ wherein R and a are defined as above and X is a halogen atom; and (B) a hydroxy compound having the general formula $R^2OH$ wherein $R^2$ is defined as above; said reacting step being carried out in the presence of (C) a polymer which includes carbon-bonded fluorine.

2. A method in accordance with claim 1 wherein component (C) is present in an amount between about 0.0001 to 100 weight parts per 100 weight part of (A).

3. A method in accordance with claim 2 wherein component (C) is present in an amount between about 0.0001 to 10 weight parts per 100 weight part of (A).

4. A method in accordance with claim 1 wherein component (C), said polymer which includes carbon-bonded fluorine, is supported on the surface of a powder.

5. A method in accordance with claim 1 wherein said reacting step is carried out at a temperature between about −78° C. and 200° C.

6. A method in accordance with claim 5 wherein said reacting step is carried out at a temperature between about 0° C. and 150° C.

7. A method in accordance with claim 1 wherein component (C), said polymer which includes carbon-bonded fluorine, is a flurohydrocarbon-siloxane copolymer.

8. A method in accordance with claim 1 wherein said reacting step is carried out at a pressure between 00001 and 10 atmospheres.

9. A method in accordance with claim 8 wherein said reacting step is carried out at a pressure between 0.001 and 3 atmospheres.

10. A method in accordance with claim 1 wherein said reacting step is carried out by feeding component (B) into a mixture of components (A) and (C).

11. A method in accordance with claim 1 wherein said reacting step is carried out by feeding components (A) and (B) into component (C).

* * * * *